US011654223B2

(12) United States Patent
Katsuki et al.

(10) Patent No.: US 11,654,223 B2
(45) Date of Patent: May 23, 2023

(54) EXTRACORPOREAL CIRCULATION MANAGEMENT DEVICE WITH BLOOD LEVEL DETECTION IN A RESERVOIR WITHOUT A SENSOR

(71) Applicant: TERUMO KABUSHIKI KAISHA, Tokyo (JP)

(72) Inventors: Ryohei Katsuki, Kanagawa (JP); Tsuyoshi Hasegawa, Kanagawa (JP); Yuuki Hara, Kanagawa (JP); Tomoaki Hashimoto, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1155 days.

(21) Appl. No.: 16/113,405

(22) Filed: Aug. 27, 2018

(65) Prior Publication Data

US 2019/0001045 A1    Jan. 3, 2019

Related U.S. Application Data

(63) Continuation of application No. PCT/JP2017/006779, filed on Feb. 23, 2017.

(30) Foreign Application Priority Data

Mar. 23, 2016   (JP) .............................. JP2016-059304

(51) Int. Cl.
    *A61M 1/36*    (2006.01)
    *G01F 23/14*   (2006.01)
    *G01F 23/18*   (2006.01)

(52) U.S. Cl.
    CPC ........ *A61M 1/3624* (2013.01); *A61M 1/3639* (2013.01); *A61M 1/3666* (2013.01);
    (Continued)

(58) Field of Classification Search
    CPC .............. A61M 1/3624; A61M 1/3639; A61M 1/3666; A61M 2206/3334; A61M 2205/3389; A61M 2205/52
    See application file for complete search history.

(56) References Cited

U.S. PATENT DOCUMENTS 6,123,519 A  *  9/2000  Kato .................... A61M 1/3632
                                                    417/395
9,044,555 B2     6/2015  Hannan
                 (Continued)

FOREIGN PATENT DOCUMENTS

EP       0766974 A2    9/1997
EP       2380611 B1   10/2011
         (Continued)

OTHER PUBLICATIONS

Bernoulli Equation, engineeringtoolbox.com/bernouilli-equation-d_183.html.*

(Continued)

*Primary Examiner* — Jessica Arble
(74) *Attorney, Agent, or Firm* — MacMillan, Sobanski & Todd, LLC (57) ABSTRACT

An extracorporeal blood circulation system monitors blood level in a reservoir which temporarily stores the blood. A memory storage unit stores blood pressure measurements from a pressure sensor monitoring a blood pressure within a tube unit conveying blood from the reservoir relative to atmosphere. A processing unit that detects a height of a top surface of the blood stored in the reservoir based on changes in the blood pressure measurements and a conservation of mechanical energy of a blood flow inside the tube unit. A notification is generated if an abnormality is detected in the height of the blood in the reservoir.

5 Claims, 10 Drawing Sheets

(52) U.S. Cl.
CPC .............. *G01F 23/14* (2013.01); *G01F 23/18* (2013.01); *A61M 2205/3334* (2013.01); *A61M 2205/3389* (2013.01); *A61M 2205/52* (2013.01)

(56) References Cited

U.S. PATENT DOCUMENTS

| | | | |
|---|---|---|---|
| 2005/0119600 A1* | 6/2005 | Lucke ................ | A61M 1/3666 604/6.15 |
| 2005/0171475 A1* | 8/2005 | Delnevo ............ | A61M 1/3624 604/119 |
| 2009/0071258 A1* | 3/2009 | Kouda ................ | A61M 1/3639 73/723 |
| 2009/0165787 A1* | 7/2009 | Ahlmen ................ | A61M 16/18 128/203.14 |
| 2015/0045712 A1 | 2/2015 | Ninomiya et al. | |
| 2016/0334261 A1* | 11/2016 | Wilson, III ......... | A61M 1/3632 |
| 2017/0089746 A1 | 3/2017 | Rossi | |

FOREIGN PATENT DOCUMENTS

| | | | |
|---|---|---|---|
| EP | 2823833 A1 | 1/2015 | |
| JP | 5735721 A | 2/1982 | |
| JP | 57113320 A | 7/1982 | |
| JP | 58087497 A | 5/1983 | |
| JP | 59163522 A | 9/1984 | |
| JP | S6116955 B2 | 5/1986 | |
| JP | S63-89712 A | 4/1988 | |
| JP | 06028134 Y * | 8/1994 | .............. A61M 1/36 |
| WO | 2015173611 A1 | 11/2015 | |

OTHER PUBLICATIONS

English translation of JP 06028134.*
PCT/JP2017/006779, International Search and Opinion Report, dated Apr. 18, 2017.
Japanese Office Action for JP Application 2018-507152 dated Feb. 19, 2021.
European Patent Search, 17769788.5 / PCTJP2017006779, dated Oct. 25, 2019.
EP-Office Action 17769788.5 dated Dec. 21, 2022.

* cited by examiner

52 RESERVOIR CROSS-SECTIONAL AREA DATA STORAGE UNIT

51 BLOOD RESERVE LEVEL CHANGE AMOUNT ESTIMATION PROCESSING UNIT (PROGRAM) (REFER TO "FLOW RATE SENSOR" AND "RESERVOIR CROSS-SECTIONAL AREA DATA STORAGE UNIT", OBTAIN "BLOOD RESERVE LEVEL CHANGE AMOUNT ESTIMATION DATA" WHICH IS CHANGE AMOUNT OF LIQUID LEVEL HEIGHT DURING PREDETERMINED TIME, ADD SAFETY MARGIN DATA OF PREDETERMINED RATIO TO "BLOOD RESERVE LEVEL CHANGE AMOUNT ESTIMATION DATA", GENERATE "MARGIN-PROVIDED BLOOD RESERVE LEVEL CHANGE AMOUNT ESTIMATION DATA" (Z Caution), AND STORE "MARGIN-PROVIDED BLOOD RESERVE LEVEL CHANGE AMOUNT ESTIMATION DATA" IN "MARGIN-PROVIDED BLOOD RESERVE LEVEL CHANGE AMOUNT ESTIMATION DATA STORAGE UNIT"

53 MARGIN-PROVIDED BLOOD RESERVE LEVEL CHANGE AMOUNT ESTIMATION DATA STORAGE UNIT (MARGIN-PROVIDED BLOOD RESERVE LEVEL CHANGE AMOUNT ESTIMATION DATA)

54 BLOOD RESERVE LEVEL ACTUAL CHANGE AMOUNT DATA GENERATION PROCESSING UNIT (PROGRAM) (REFER TO "BLOOD RESERVE LEVEL ESTIMATION DATA STORAGE UNIT", CALCULATE "BLOOD RESERVE LEVEL ACTUAL CHANGE AMOUNT DATA", BASED ON "BLOOD RESERVE LEVEL ESTIMATION DATA", SERVING AS LENGTH (HEIGHT) (zx-zy) BETWEEN PLURALITY OF LIQUID LEVELS (x) AND PRESSURE MEASUREMENT POINT (y), AND TIME DATA THEREOF, AND STORE "BLOOD RESERVE LEVEL ACTUAL CHANGE AMOUNT DATA" IN "BLOOD RESERVE LEVEL ACTUAL CHANGE AMOUNT DATA STORAGE UNIT"

55 BLOOD RESERVE LEVEL ACTUAL CHANGE AMOUNT DATA STORAGE UNIT (BLOOD RESERVE LEVEL ACTUAL CHANGE AMOUNT DATA (Δ(zx-zy)))

56 BLOOD RESERVE LEVEL CHANGE AMOUNT ABNORMALITY DETERMINATION PROCESSING UNIT (PROGRAM) (REFER TO "BLOOD RESERVE LEVEL ACTUAL CHANGE AMOUNT DATA STORAGE UNIT" AND "MARGIN-PROVIDED BLOOD RESERVE LEVEL CHANGE AMOUNT ESTIMATION DATA STORAGE UNIT", DETERMINE WHETHER OR NOT "BLOOD RESERVE LEVEL ACTUAL CHANGE AMOUNT DATA" FALLS WITHIN OR BEYOND RANGE OF "MARGIN-PROVIDED BLOOD RESERVE LEVEL CHANGE AMOUNT ESTIMATION DATA", AND IN CASE OF BEYOND, OUTPUT "WARNING / ALARM" TO TOUCH PANEL

EXTRACORPOREAL CIRCULATION MANAGEMENT DEVICE WITH BLOOD LEVEL DETECTION IN A RESERVOIR WITHOUT A SENSOR

CROSS REFERENCE TO RELATED APPLICATIONS

This application is a continuation of PCT Application No. PCT/JP2017/006779, filed Feb. 23, 2017, based on and claiming priority to Japanese Application No. 2016-059304, filed Mar. 23, 2016, both of which are incorporated herein by reference in their entirety.

BACKGROUND OF THE INVENTION

The present invention relates to an extracorporeal circulation management device, an extracorporeal circulator, an extracorporeal circulation management system, an extracorporeal circulation management program, and a control method of an extracorporeal circulation management device, for example, which are used in order to manage blood extracorporeal circulation where blood of a patient is supplied through gas exchange.

BACKGROUND ART

In the related art, for example, as an extracorporeal circulation technique, a cardiopulmonary support technique has been used by an artificial heart lung machine (extracorporeal circulator) using a centrifugal pump and a membrane type artificial lung during open heart surgery.

In some cases, this extracorporeal circulator includes a blood reserve tank (reservoir) which temporarily stores removed blood before gas exchange is performed on the artificial lung for the blood removed from a patient. This reservoir temporarily reserves the removed blood in order to remove bubbles mixed into the blood. That is, a configuration is adopted as follows. The blood reserved inside the reservoir is sequentially supplied to the artificial lung, and the blood subjected to the gas exchange is returned to an artery of the patient.

However, after all of the blood stored inside the reservoir is returned to circulation, and if a blood supply operation is subsequently performed with an empty reservoir, air is supplied into a body of the patient via the artificial lung, thereby bringing the patient into an extremely hazardous condition. Therefore, a technique using a level sensor has been proposed in order to recognize the presence or absence of blood inside the reservoir (for example, EP2380611B1).

However, the reservoir is used in order to store the blood of the patient, and after being drawn from the reservoir the blood is again provided to the patient after gas exchange is performed in the artificial lung. Therefore, when the level sensor is located in the reservoir, there is a problem from a viewpoint of hygienic considerations.

Therefore, an object of the present invention is to provide an extracorporeal circulation management device, an extracorporeal circulator, an extracorporeal circulation management system, an extracorporeal circulation management program, and a control method of an extracorporeal circulation management device, which enable a user to hygienically and precisely recognize a change in the level of blood inside a blood reserve tank such as a reservoir without locating a sensor in the blood reserve tank.

SUMMARY OF THE INVENTION

According to the present invention, the above-described object is realized by an extracorporeal circulation management device having a processing unit that generates blood reserve change information serving as information on change in the blood amount in a blood reserve unit, based on pressure change information serving as information on change in pressure in a pressure measurement unit which is located in a tube unit (e.g., plastic tubing for carrying blood from an output of the blood reserve unit) and exposed to atmosphere, and which measures the pressure of the blood inside the tube unit.

According to the invention, based on the pressure change information (for example, information on change in the pressure value of a pressure sensor) of the pressure measurement unit such as the pressure sensor which is located in the tube unit such as a tube for guiding the blood extending from the blood reserve unit such as the reservoir, and which measures the pressure of the blood inside the tube unit, it is possible to generate the blood reserve change information (for example, information on change in the distance (height) between the liquid level of the reservoir and the pressure measurement point) on the blood amount in the blood reserve unit. Therefore, it is possible to hygienically and precisely recognize a change amount of the blood inside the blood reserve unit without locating a sensor in the blood reserve unit.

Preferably, the extracorporeal circulation management device further has an electronic memory storage unit that stores information on the density of the blood, gravitational acceleration information, measurement unit flow velocity information serving as flow velocity information output from a flow rate measurement unit which is located in the tube unit for guiding the blood from the blood reserve unit so as to measure a flow rate of the blood inside the tube unit, and measurement unit pressure information serving as pressure information output from the pressure measurement unit. Preferably, the processing unit performs calculations by comparing liquid level energy information having the density information in the liquid level, the gravitational acceleration information, liquid level flow velocity information serving as the flow velocity information in the liquid level of the blood in the blood reserve unit, and liquid level pressure information serving as the pressure information in the liquid level, with measurement unit energy information having the measurement unit flow velocity information, the measurement unit pressure information, the density information, and the gravitational acceleration information so as to obtain difference information between liquid level height information serving as height information in the liquid level and measured blood height information serving as height information in the measured blood.

According to a preferred embodiment, the calculation is performed by comparing the liquid level energy information having the density information in the liquid level, the gravitational acceleration information, the liquid level flow velocity information, and the liquid level pressure information, with the measurement unit energy information having the measurement unit flow velocity information, the measurement unit pressure information, the density information, and the gravitational acceleration information. In this manner, a configuration is adopted so as to obtain the difference information (for example, (zx−zy)) between the liquid level height information (for example, (zx)) and the measured blood height information (for example, (zy)).

"Bernoulli's theorem" is the law of conservation of mechanical energy in a steady flow of a non-compressible and non-adherent liquid. It states that the "liquid level energy information" derived from the "density information at the liquid level", the "gravitational acceleration information", the "liquid level flow velocity information", the "liquid level pressure information" and the "liquid level height information", and the measurement unit energy information" derived from the "measurement unit flow velocity information", the "measurement unit pressure information", the "density information", the "gravitational acceleration information", and the "measured blood height information" are constant.

Therefore, in preferred embodiments, the calculation is performed by comparing the "liquid level energy information" and the "measurement unit energy information" with each other. In this manner, it is possible to easily and accurately obtain the difference information between the "liquid level height information" and the "measured blood height information".

In particular, for example, as to the "liquid level energy information", the "density information at the liquid level", the "gravitational acceleration information", the "liquid level flow velocity information", and the "liquid level pressure information" are already known, and as to the "measurement unit energy information", the "density information" and the "gravitational acceleration information" are already known. Thus, if a relational expression between the "measurement unit flow velocity information" and the "liquid level flow velocity information" is already known, the difference information between the "liquid level height information" and the "measured blood height information", that is, the information on change in the height of the liquid level can be obtained based on the change information on the pressure information on the remaining "measurement unit pressure information". In this way, it is possible to hygienically and precisely recognize the change amount of the blood inside the blood reserve unit without locating the sensor in the blood reserve unit.

Preferably, the blood reserve change information is generated, based on pressure loss coefficient information obtained from the liquid level to the pressure measurement unit.

According to the preferred embodiment, the blood reserve change information is generated, based on the pressure loss coefficient information obtained from the liquid level to the pressure measurement unit. Therefore, the blood reserve change information on the blood amount in the blood reserve unit, for example, the information on change in the height of the liquid level can be more accurately recognized.

Preferably, corrected pressure loss coefficient information is generated, based on a plurality of change information items of the pressure loss coefficient in time series, and the blood reserve change information is generated, based on the corrected pressure loss coefficient information.

According to the preferred embodiment, the corrected pressure loss coefficient information is generated, based on a plurality of the change information items of the pressure loss coefficient in time series, and the blood reserve change information is generated, based on the corrected pressure loss coefficient information. Therefore, for example, even if a pressure loss coefficient in a circuit or a flow path in the extracorporeal circulator is changed, for example, during a medical procedure, a health care worker can generate average corrected pressure loss coefficient information, based on a plurality of the change information items in time series. Therefore, the blood reserve change information can be generated, based on the corrected pressure loss coefficient information. In this manner, the accuracy can be further improved.

Preferably, based on a plurality of the blood reserve change information items, the presence or absence of occurrence of changed abnormality information serving as abnormality information indicating a change in a plurality of the blood reserve change information items is determined, and the occurrence of abnormality is notified when abnormality occurs.

According to the preferred embodiment, based on a plurality of the blood reserve change information items, the presence or absence of occurrence of the changed abnormality information serving as the abnormality information indicating the change in a plurality of the blood reserve change information items is determined, and the occurrence of abnormality is notified when abnormality occurs. That is, for example, in some cases, the tube unit such as the plastic tubing conveying the blood may be squeezed (constricted) with forceps in order to adjust the flow rate in an intermediate portion of a circuit of the extracorporeal circulator. In this case, information relating to the pressure loss coefficient is changed, and thus, it becomes difficult to generate accurate blood reserve change information. Therefore, according to a preferred embodiment, in order to generate the accurate blood reserve change information, it is possible to notify the occurrence of abnormality and to prompt a user to change the information relating to the pressure loss coefficient.

Preferably, an extracorporeal circulator has the blood reserve unit, the tube unit, the pressure measurement unit, an artificial lung unit that performs gas exchange on the blood of a target person, and the extracorporeal circulation management device.

Preferably, an extracorporeal circulation management system includes a management device connected to and communicable with the extracorporeal circulation management device, and the extracorporeal circulator.

According to the present invention, the above-described object is realized by an extracorporeal circulation management program for causing an extracorporeal circulation management device to function as a processing unit that generates blood reserve change information serving as information on change in a blood amount in a blood reserve unit, based on pressure change information serving as information on change in pressure in a pressure measurement unit which is located in a tube unit for guiding blood extending from the blood reserve unit reserving the blood and exposed to atmosphere, and which measures the pressure of the blood inside the tube unit.

According to the present invention, the above-described object is realized by a control method of an extracorporeal circulation management device. The device includes generating blood reserve change information serving as information on change in a blood amount in a blood reserve unit, based on pressure change information serving as information on change in pressure in a pressure measurement unit which is located in a tube unit for guiding blood extending from the blood reserve unit reserving the blood and exposed to atmosphere, and which measures the pressure of the blood inside the tube unit.

As described above, according to the present invention, there are advantageous effects as follows. It is possible to provide an extracorporeal circulation management device, an extracorporeal circulator, an extracorporeal circulation management system, an extracorporeal circulation management program, and a control method of an extracorporeal circulation management device, which enable a user to hygienically and precisely recognize a change in blood inside a blood reserve tank such as a reservoir without locating a sensor in the blood reserve tank.

BRIEF DESCRIPTION OF THE DRAWINGS

FIG. 5 is a schematic block diagram illustrating a main configuration of a third various information storage unit.

DETAILED DESCRIPTION OF PREFERRED EMBODIMENTS

Hereinafter, preferred embodiments according to the present invention will be described in detail with reference to the accompanying drawings. The embodiments described below are preferable specific examples according to the present invention. Therefore, the embodiments have various technically preferable limitations. However, the scope of the present invention is not limited to the aspects unless the present invention is particularly limited in the following description.

Figure 1:
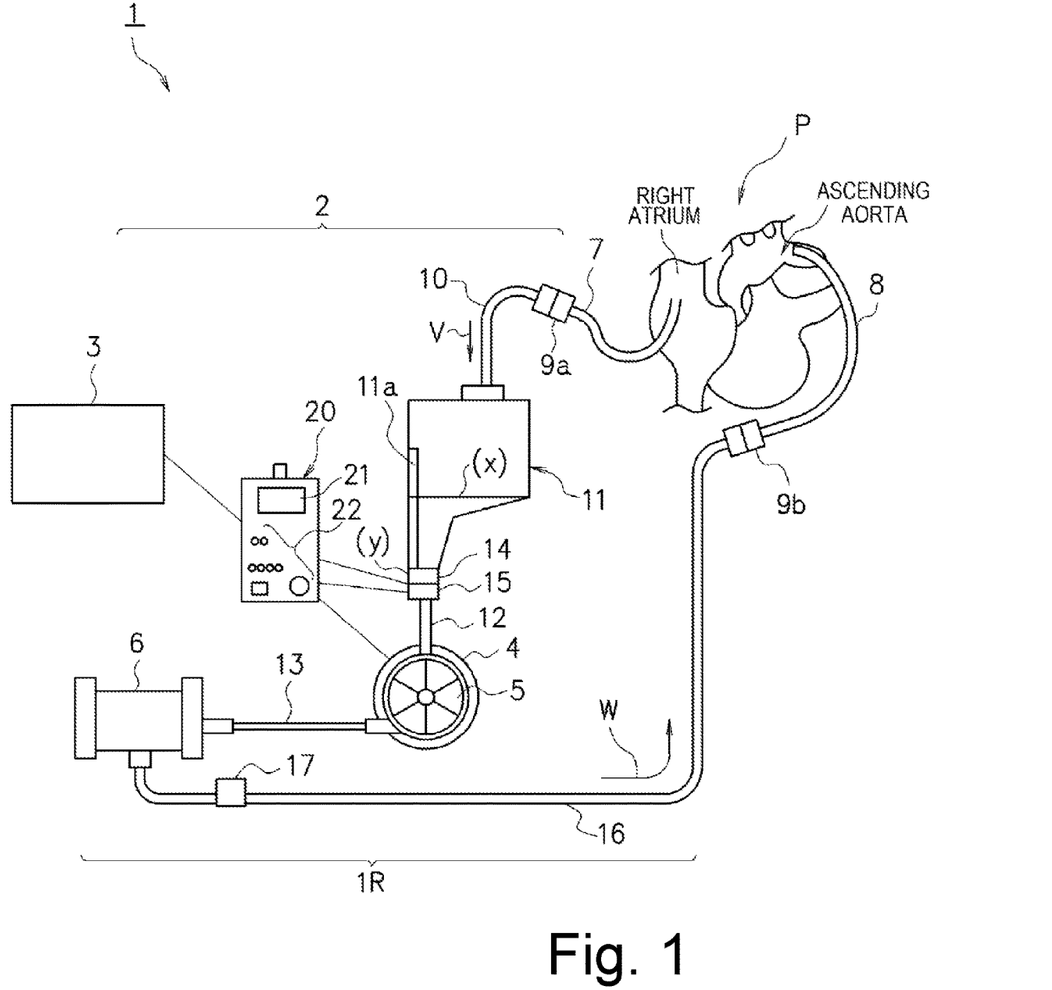
FIG. 1 is a schematic view illustrating a main configuration of an extracorporeal circulation system according to an embodiment of the present invention.

FIG. 1 is a schematic view illustrating a main configuration of an extracorporeal circulation system 1 according to an embodiment of the present invention. The extracorporeal circulation system 1 illustrated in FIG. 1 performs extracorporeal circulation on blood of a patient P, for example, who is a target person illustrated in FIG. 1. When the extracorporeal circulation system 1 is used, in some cases, it is considered that the heart of the patient P is not functioning normally, or the heart is functioning normally but the lung is not functioning normally.

Incidentally, the extracorporeal circulation system 1 illustrated in FIG. 1 according to the present embodiment has an extracorporeal circulator 2 illustrated in FIG. 1, for example, which is used in a case where cardiac surgery is performed on the patient P or in a case of subsequent treatment in an intensive care unit (ICU), and a management server 3, for example, which is a management device connected to and communicable with a controller 20, for example, which is an extracorporeal circulation management device (to be described later) belonging to the extracorporeal circulator 2. This management server 3 is used in order to manage each controller 20 of a plurality of extracorporeal circulators 2 arranged in an ICU.

Specifically, the management server 3 is configured to manage various information items relating patients or drugs, and to provide each controller 20 with required information relating to the patients or the drugs, if necessary. In addition, in the present embodiment, an example will be described below where the controller 20 mainly performs processing on various information items. However, the present invention is not limited thereto. Instead of the controller 20, the management server 3 may perform the processing on various Information items.

Next, a configuration of the extracorporeal circulator 2 illustrated in FIG. 1 will be described. The extracorporeal circulator 2 uses a "drive motor 4" to operate a "centrifugal pump 5", removes blood from a vein (vena cava) of the patient P, performs gas exchange in the blood by using an artificial lung 6, for example, which is an artificial lung unit, and performs oxygenation of the blood. Thereafter, the extracorporeal circulator 2 performs "artificial lung extracorporeal blood circulation" for returning the blood again to an artery (aorta) of the patient P. That is, the extracorporeal circulator 2 functions as a substitution for the heart and the lung.

That is, as illustrated in FIG. 1, the extracorporeal circulator 2 has a "circulation circuit 1R" for circulating the blood, and the circulation circuit 1R has the "artificial lung 6", the "centrifugal pump 5", the "drive motor 4", a "venous cannula (blood removal side cannula) 7", an "arterial cannula (blood supply side cannula) 8", and the controller 20.

The venous cannula (blood removal side cannula) 7 illustrated FIG. 1, a distal end of the venous cannula 7 is caused to indwell a right atrium of the heart of the patient P via a connector 9a. On the other hand, the arterial cannula (blood supply side cannula) 8 is inserted into an ascending aorta of the heart of the patient P via a connector 9b illustrated FIG. 1. The venous cannula 7 is connected to a reservoir 11, for example, which is a blood reserve unit via a connector 9a by using a blood removal tube 10, for example, which is a tube unit typically formed of a transparent plastic material.

This reservoir 11 is configured to reserve (i.e., temporarily store) the blood on the vein side of the patient P. This reservoir 11 is located to remove air bubbles inside the blood received mainly from the blood removal tube 10. In addition, as illustrated in FIG. 1, the reservoir 11 is formed so that a cross-sectional area on an upper side is larger than a cross-sectional area on a lower side, and has a shape which is gradually tapers from the upper side to the lower side. In addition, the reservoir 11 is exposed to atmosphere so that atmospheric pressure is applied to the upper surface of the blood reserved therein. Furthermore, scale markings 11a, which can be compared with the liquid level of the blood reserved therein, are formed on a side surface of the reservoir 11.

In this way, the blood from which the air bubbles are removed in the reservoir 11 is conveyed to the centrifugal pump 5 via a "first intermediate tube 12", for example, which is the tube unit in FIG. 1, and is further connected to the artificial lung 6 via a "second intermediate tube 13", for example, which is also a tube unit. Incidentally, a pressure sensor 14, for example, which is a pressure measurement unit for measuring pressure of the blood supplied from the reservoir 11, and a flow rate sensor 15, for example, which is a flow rate measurement unit for measuring a flow rate are arranged in the first intermediate tube 12, and each are configured so as to measure the blood supplied from the reservoir 11.

In addition, the blood subjected to gas exchange in the artificial lung 6 is supplied to the arterial cannula 8 via a blood supply tube 16, which is, for example, a tube unit, and the connector 9b. An arterial filter 17 for removing the air bubbles is located in the blood supply tube 16.

In addition, the controller 20 is connected to communicate with the pressure sensor 14, the flow rate sensor 15, and the drive motor 4. Therefore, the controller 20 can acquire measurement value information of the pressure sensor 14 or the flow rate sensor 15, and is configured to be capable of transmitting a drive signal to the drive motor 4. Therefore, the controller 20 is configured to control the rotation of the centrifugal pump 5 via the drive motor 4.

As illustrated in FIG. 1, the controller 20 includes a "touch panel 22" which displays various information items, which can input various information items, and which is formed of color liquid crystal or organic EL, and an "input device 22" for inputting various information items.

In addition, the artificial lung 6 illustrated in FIG. 1 performs a gas exchange operation (oxygen addition and/or carbon dioxide removal) on the blood. For example, the artificial lung 6 is a membrane type artificial lung. However, particularly preferably a hollow fiber membrane type artificial lung is used. Inside the blood removal tube 10, the blood flows in a direction V, and inside the blood supply tube 16, the blood flows in a direction W.

Incidentally, the controller 10 or the management server 3 of the extracorporeal circulator 1 illustrated in FIG. 1 has a computer, and the computer has a central processing unit (CPU), a random access memory (RAM), and a read only memory (ROM) which are not illustrated. These are connected to each other via a bus.

Figure 2:
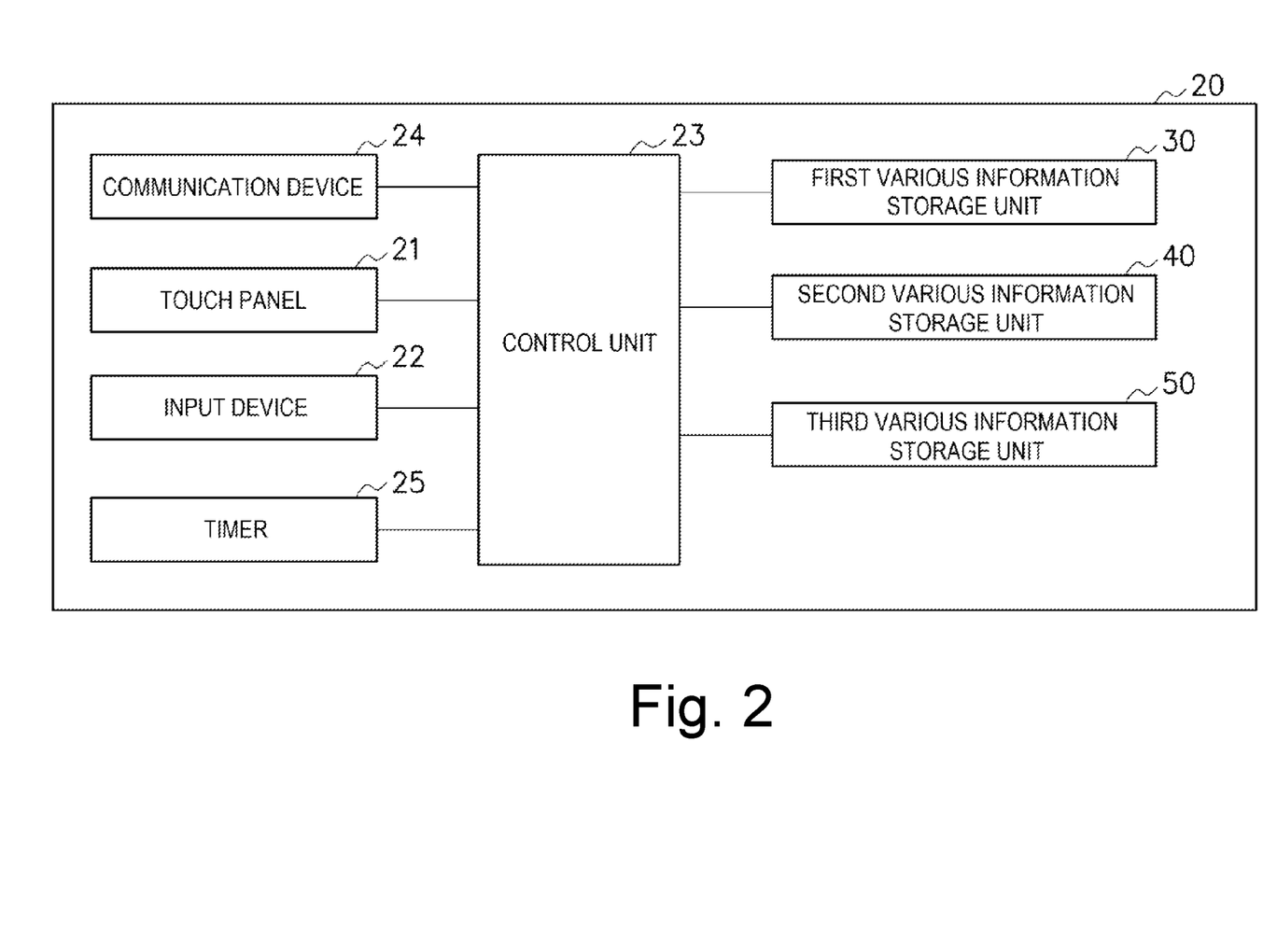
FIG. 2 is a schematic block diagram illustrating a main configuration of a controller of an extracorporeal circulator in FIG. 1.

FIG. 2 is a schematic block diagram illustrating a main configuration of the controller 20 of the extracorporeal circulator 2 illustrated in FIG. 1. As illustrated in FIG. 2, the controller 20 has a "control unit 23", and the control unit 23 controls the drive motor 4, the pressure sensor 14, and the flow rate sensor 15 which are illustrated in FIG. 1, a "communication device 24" for communicating with other devices. In addition, the control unit 23 also controls the touch panel 22, the input device 22, and a timer 25.

Figure 3:
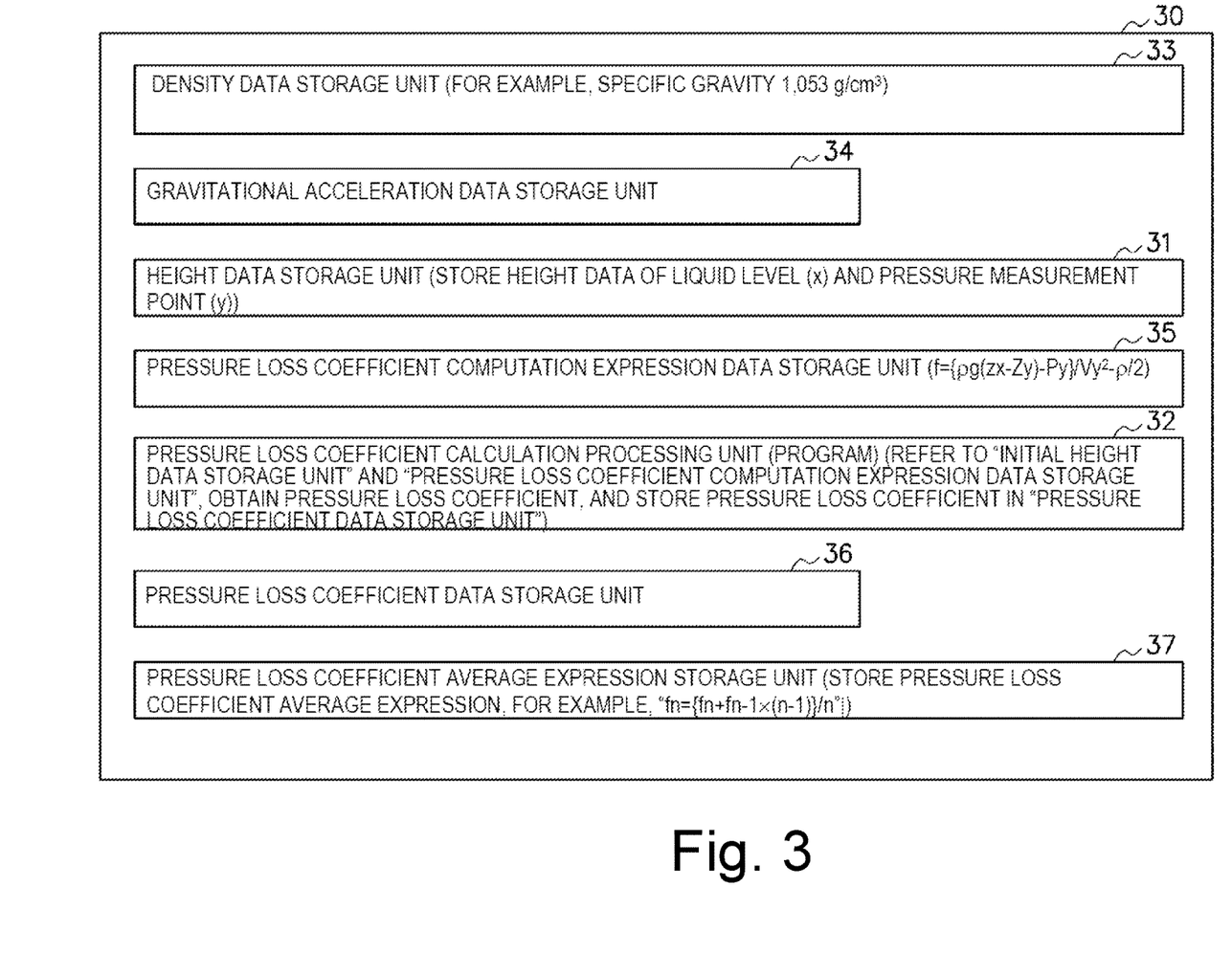
FIG. 3 is a schematic block diagram illustrating a main configuration of a first various information storage unit.
Figure 4:
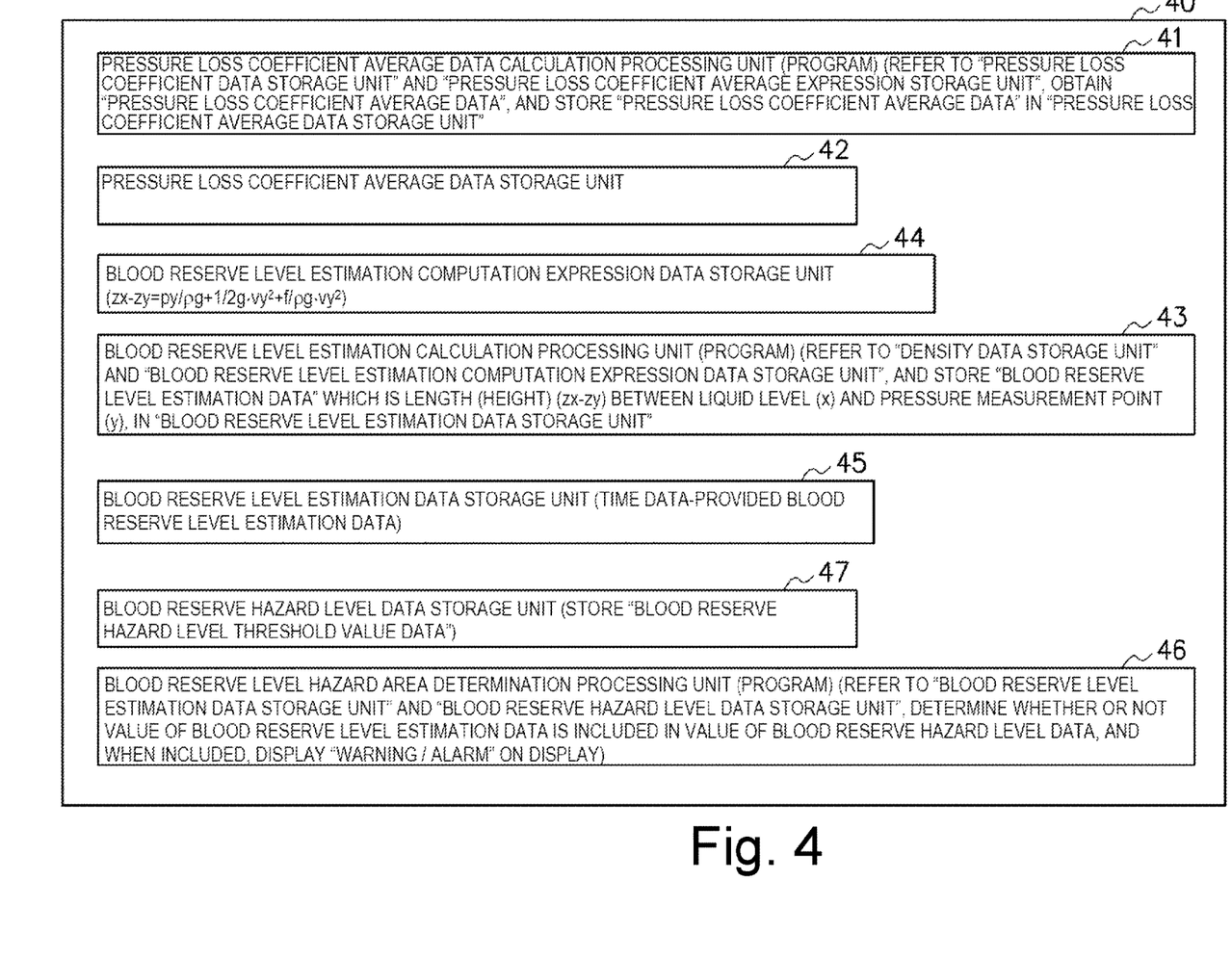
FIG. 4 is a schematic block diagram illustrating a main configuration of a second various information storage unit.
Figure 6:
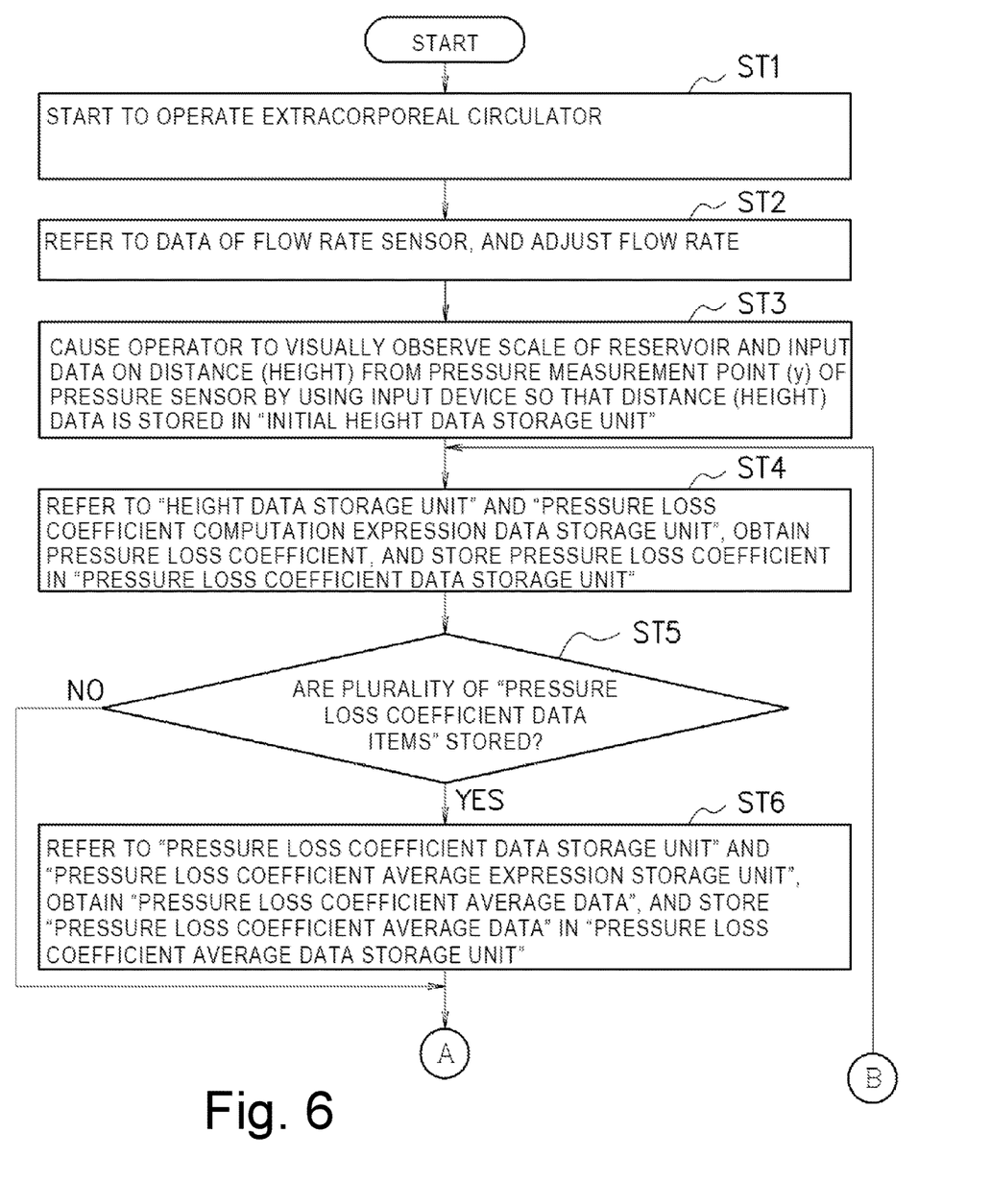
FIG. 6 is a flowchart illustrating a main operation example of the extracorporeal circulator in FIG. 1.
Figure 7:
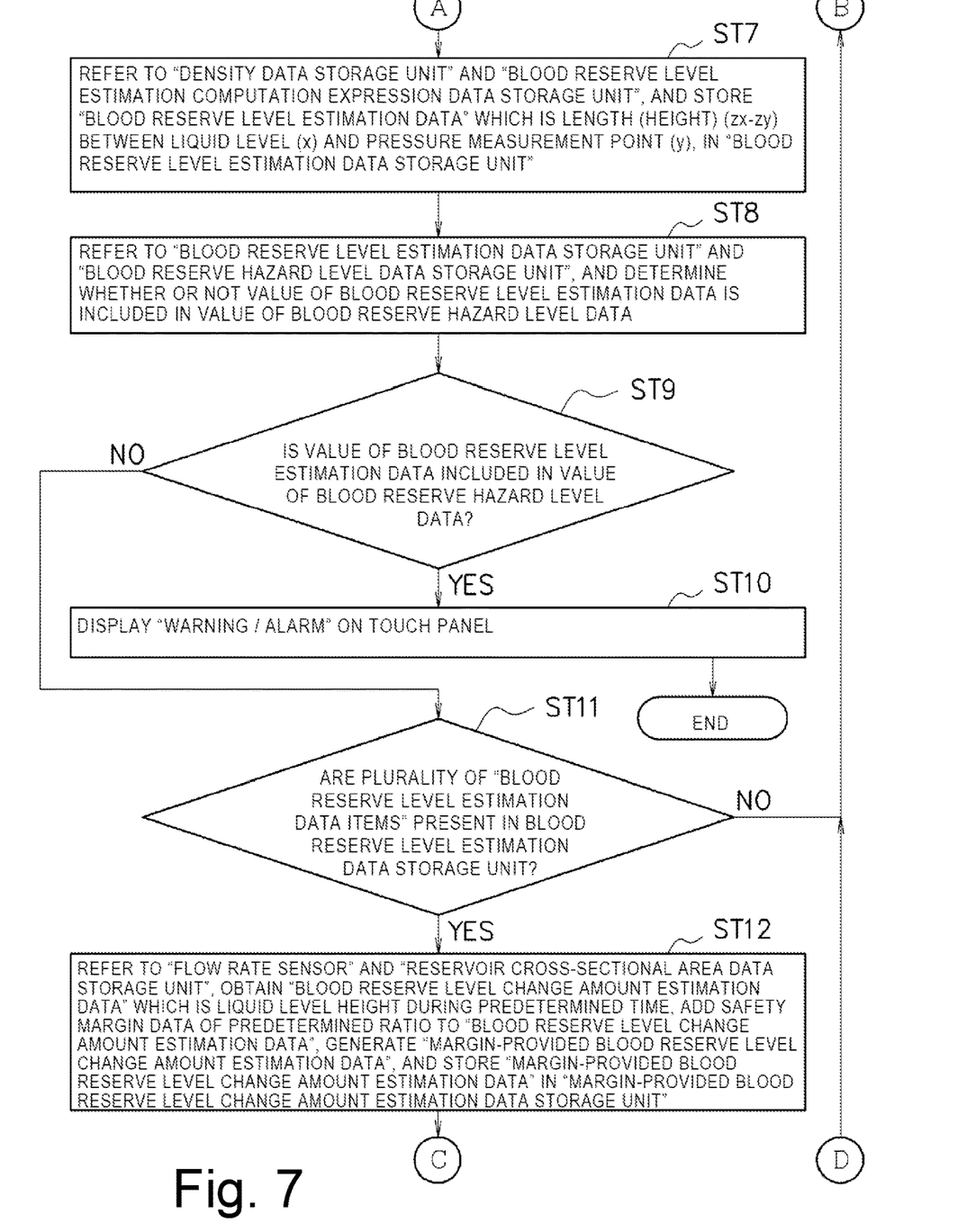
FIG. 7 is a flowchart illustrating a main operation example of the extracorporeal circulator in FIG. 1.
Figure 8:
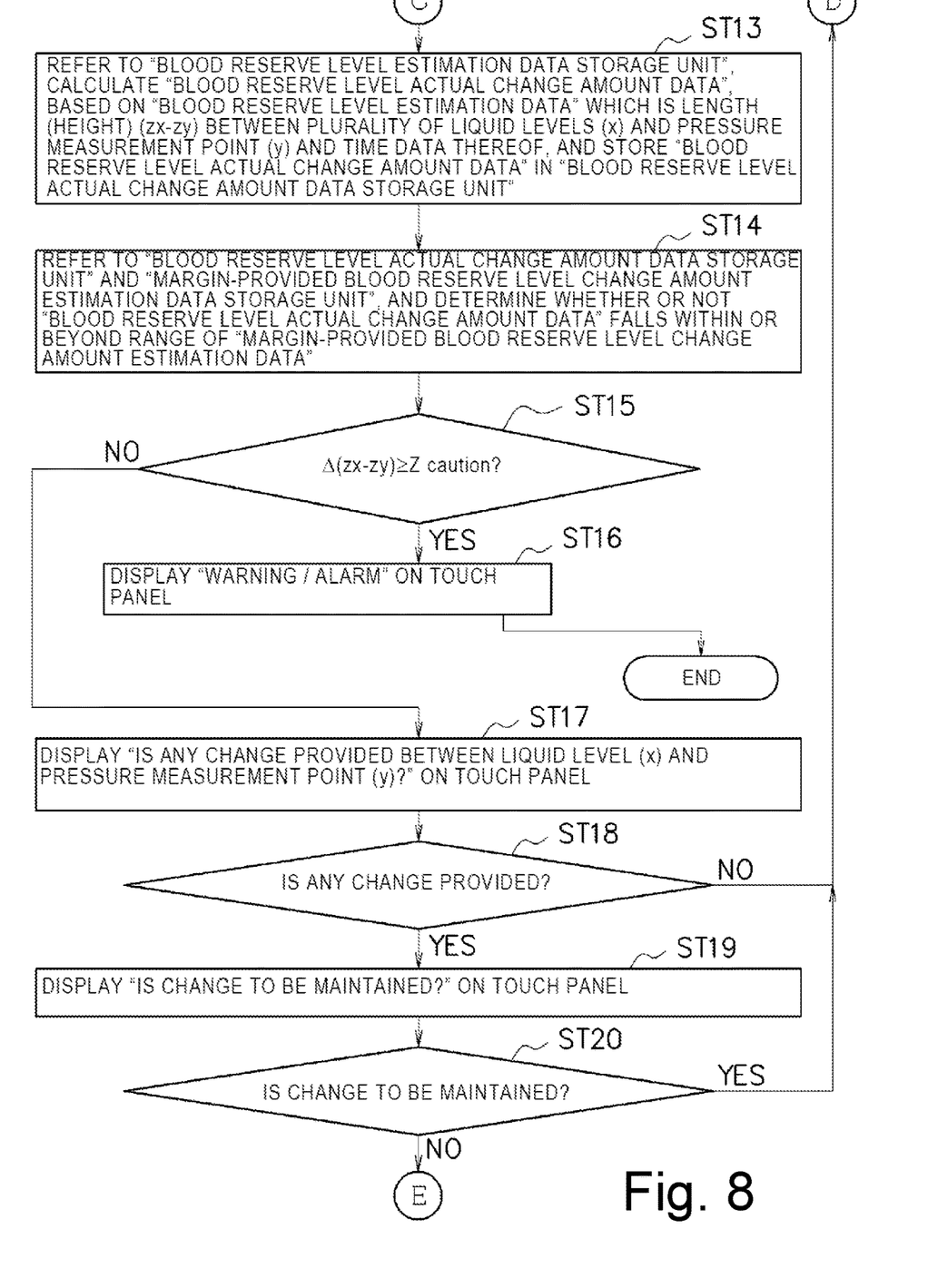
FIG. 8 is a flowchart illustrating a main operation example of the extracorporeal circulator in FIG. 1.
Figure 9:
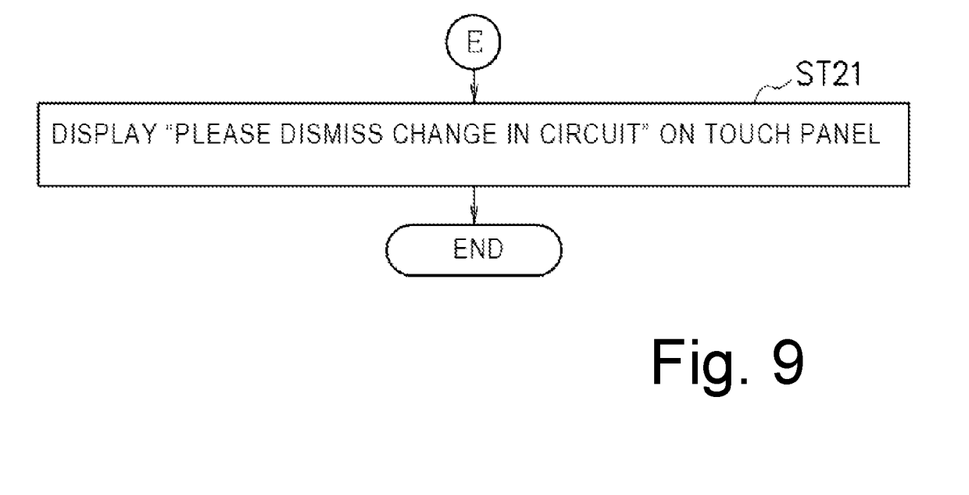
FIG. 9 is a flowchart illustrating a main operation example of the extracorporeal circulator in FIG. 1.

Furthermore, the control unit 23 controls a "first various information storage unit 30", a "second various information storage unit 40", and a "third various information storage unit 50" which are illustrated in FIG. 2. FIGS. 3 to 5 are respectively schematic block diagrams illustrating preferred configurations of the "first various information storage unit 30", the "second various information storage unit 40", and the "third various information storage unit 50". These contents will be described later.

FIGS. 6 to 9 are schematic flowcharts illustrating a main operation example of the extracorporeal circulator 2 in FIG. 1. Hereinafter, description will be made with reference to these flowcharts, and the configurations in FIGS. 1 to 5 will be described. First, in a step 1 of FIG. 6 (hereinafter, referred to as "ST") 1, the extracorporeal circulator 2 illustrated in FIG. 1 starts to perform an operation. Specifically, the blood of the patient P is introduced into the reservoir 11 via the venous cannula 7 and the blood removal tube 10, and the blood reserved inside the reservoir 11 is supplied to the artificial lung 6 through the centrifugal pump 5 driven by the drive motor 4 illustrated in FIG. 1.

Next, the process proceeds to ST2. In ST2, an operator refers to data of the flow rate sensor 15, and adjusts a flow rate. Next, the process proceeds to ST3. In ST3, the operator visually observes the scale 11a of the reservoir 11 illustrated in FIG. 1, and inputs data on distance (height) from the pressure measurement point (y) of the pressure sensor 14, that is, data on the distance (height) between the pressure sensor 14 and the liquid level (x) of the blood reserved inside the reservoir 11, by using the input device 22. Then, the distance (height) data is stored in a "height data storage unit 31" illustrated in FIG. 3. The stored data provides an initial reference for tracking changes in the height of the liquid level.

Next, the process proceeds to ST4. In ST4, a "pressure loss coefficient calculation processing unit (program) 32" in FIG. 3 is performed, in reliance on the "height data storage unit 31", a "density data storage unit 33", a "gravitational acceleration data storage unit 34", the "flow rate sensor 15", the "pressure sensor 14", and a "pressure loss coefficient computation expression data storage unit 35". A pressure loss coefficient, for example, which is pressure loss coefficient information between the liquid level (x) of the reservoir 11 in FIG. 1 and the pressure measurement point (y) of the pressure sensor 14 is obtained and stored in a "pressure loss coefficient data storage unit 36".

That is, in this step, a "pressure loss" within a portion of a perfusion circuit (the reservoir 11, the first intermediate tube 12, and the pressure sensor 14) between the liquid level (x) and the pressure measurement point (y) in FIG. 1 is obtained and stored in the "pressure loss coefficient data storage unit 36". An expression of $$f = \frac{\rho g(zx - zy) - py}{vy2} - \frac{\rho}{2}$$

stored in the "pressure loss coefficient computation expression data storage unit 35" used in this case will be described below.

With regard to energy of a liquid, "Bernoulli's theorem" is known. The theorem provides a "law of conservation of energy in a steady flow of a non-compressible and non-adherent liquid". Specifically, a value of "p(fluid pressure)/ρ(fluid density)+g(gravitational acceleration)×z(vertical height)+v2(flow velocity)/2" is constant.

The energy at the liquid level (x) inside the reservoir 11 in FIG. 1 is expressed by the following expression where ρ is density, v is flow velocity, p is pressure, g is gravitational acceleration, and z is height", and the energy at the liquid level (x) of the blood in the reservoir 11 is expressed by $$\frac{1}{2\rho vx2} + px + \rho gzx.$$

On the other hand, the energy at the pressure measurement point (y) of the pressure sensor 14 is expressed by $$\frac{1}{2\rho vy2} + py + \rho gzy.$$

In addition, according to the "Bernoulli's theorem" described above, "the energy (an example of the liquid level energy information) of the liquid level (x) in the reservoir 11" and "the energy (an example of the measurement unit energy information) at the pressure measurement point (y) of the pressure sensor 14" are the same as each other, and, the following expression is obtained:

$$\frac{1}{2\rho vx2} + px + \rho gzx = \frac{1}{2\rho vy2} + py + \rho gzy \qquad \text{(Expression 1)}$$

Here, "vx (flow velocity)" in the liquid level (x) in the reservoir 11 is different from "vy (flow velocity)" at the pressure measurement point (y) of the pressure sensor 14, and "vx<vy" is satisfied. Therefore, the following correction is performed:

$$1/2\rho(vy2-vx2) \cong 1/2\rho vy2 \quad \text{(Expression 2)}$$

That is, "vx (flow velocity)" in the liquid level (x) in the reservoir 11 is set to substantially "0". The "flow velocity vx" expressed by "$1/2\rho(vy2-vx2) \cong 1/2\rho vy2$" is an example of the "liquid level flow velocity information".

In addition, the pressure (px) in the liquid level (x) in the reservoir 11 is measured by relative pressure. Accordingly, the atmospheric pressure is set to "0". That is, "px=0" is satisfied (Expression 3). This expression, "px=0" is an example of the "liquid level pressure information".

Here, if "Expression 2" and "Expression 3" are combined with "Expression 1", and if "Expression 1" is transformed into an expression for obtaining "zx−zy", then $$zx - zy = \frac{vy2}{2g} + \frac{py}{\rho g} \quad \text{(Expression 4)}$$

is satisfied. That is, if the gravitational acceleration (g) and ρ (density) are known, a height change in the liquid level (x) can be recognized using a change in "py" (i.e., pressure at the pressure measurement point (y)), which is an example of the pressure change information.

However, in actual practice, there exists a pressure loss (f) which cannot be ignored due to a flow path between the liquid level (x) and the pressure measurement point (y). Accordingly, it is necessary to add a term of the "pressure loss" in proportion to the square of the flow velocity (v). Therefore, (Expression 4) is transformed into an expression for obtaining the pressure, and the term of the pressure loss is introduced wherein "f" is the pressure loss coefficient (depending on a circuit or a flow path), as follows:

$$py = \rho g(zx - zy) - \frac{\rho}{2vy2} - fvy2 \quad \text{(Expression 5)}$$

According to the present embodiment, as will be described later, the pressure loss is obtained using a computation expression. However, the present invention is not limited thereto. The pressure loss at the "liquid level (x) in the reservoir 11" and the "measurement point (y) of the pressure sensor 14" may be fixed to each other.

Next, if (Expression 5) including the term of the pressure loss is transformed into an expression for obtaining "zx−zy", an "expression for estimating a blood reserve level" is obtained as follows:

$$zx - zy = \frac{py}{\rho g} + \frac{1}{2g}vy2 + \frac{f}{\rho g}vy2 \quad \text{(Expression 6)}$$

Next, if this (Expression 6) is transformed into an expression for obtaining "f (pressure loss coefficient)", then $$f = \frac{\rho g(zx - zy) - py}{vy2} - \frac{\rho}{2}$$

is satisfied so as to obtain "pressure loss coefficient computation expression data" of the above-described "pressure loss coefficient computation expression data storage unit 35" in FIG. 3.

In ST4, after the "pressure loss coefficient" is obtained and stored in the "pressure loss coefficient data storage unit 36" in FIG. 3, the process proceeds to ST 5. In ST5, it is determined whether or not a plurality of the "pressure loss coefficient data items" are stored in the "pressure loss coefficient data storage unit 36" in FIG. 3.

In ST5, if a plurality of the "pressure loss coefficient data items" are stored, the process proceeds to ST6. In ST6, a "pressure loss coefficient average data calculation processing unit (program) 41" in FIG. 4 is performed so as to refer to the "pressure loss coefficient data storage unit 36" and a "pressure loss coefficient average expression storage unit 37" in FIG. 3.

A pressure loss coefficient average expression, for example, "$f_n = \{f_n + f_{n-1} \times (n-1)\}/n$" is stored in the "pressure loss coefficient average expression storage unit 37". Therefore, "pressure loss coefficient average data" is obtained by substituting the "pressure loss coefficient data" into the "pressure loss coefficient average expression", and is stored in a "pressure loss coefficient average data storage unit 42" in FIG. 4.

This "pressure loss coefficient average data" is an example of the "corrected pressure loss coefficient information". Therefore, for example, even if the pressure loss coefficient in the circuit or the flow path in the extracorporeal circulator 2 is changed during a medical procedure, based on a plurality of change information items in time series, a health care worker can generate more accurate "pressure loss coefficient average data".

Next, the process proceeds to ST7. In ST7, a "blood reserve level estimation calculation processing unit (program) 43 (an example of the processing unit)" in FIG. 4 is performed so as to refer to the "density data storage unit 33", for example, which shows the density information in FIG. 3, the "gravitational acceleration data storage unit 34", for example, which shows the gravitational acceleration information, the "flow rate sensor 15 (an example of the measurement unit flow velocity information)", the "pressure sensor 14 (an example of the measurement unit pressure information)", the "pressure loss coefficient data storage unit 36", or the "pressure loss coefficient average data storage unit 42" and a "blood reserve level estimation computation expression data storage unit 44" which are illustrated in FIG. 4.

An expression $$zx - zy = \frac{py}{\rho g} + \frac{1}{2g}vy2 + \frac{f}{\rho g}vy2$$

which is the same as (Expression 6) serving as the above-described "expression for estimating the blood reserve level" is stored in the "blood reserve level estimation computation expression data storage unit 44". Therefore, data of the "density data storage unit 33", the "gravitational acceleration data storage unit 34", the "flow rate sensor 15", the "pressure sensor 14", the "pressure loss coefficient data storage unit 36", or the "pressure loss coefficient average data storage unit 42" in FIG. 4 is substituted into the above-described expression, and calculation is performed. In this manner, it is possible to obtain the distance (height) between the liquid level (x) in the reservoir 11, for example, which is the liquid level height information, and the pressure measurement point (y), for example, which is about the blood measured with the pressure sensor 14 and which is the measured blood height information, that is, "zx−zy (an example of the difference information and the blood reserve change information)".

Then, the distance (height), that is, "zx−zy" between the liquid level (x) in the reservoir 11 and the pressure measurement point (y) of the pressure sensor 14 is stored as "blood reserve level estimation data" together with the measured time data in a "blood reserve level estimation data storage unit 45". In this case, as the data of the pressure loss coefficient (f), the data of the "pressure loss coefficient average data storage unit 42" in FIG. 4 is used instead of the data of the "pressure loss coefficient data storage unit 36", thereby further improving the accuracy in estimating the blood reserve level.

In this way, according to the present embodiment, the change in the distance (height), that is, the change in "zx−zy" between the liquid level (x) in the reservoir 11 and the pressure measurement point (y) of the pressure sensor 14 can be accurately recognized using the change in the measurement value of the pressure sensor 14. Accordingly, it is possible to hygienically and precisely recognize the change amount of the blood inside the reservoir 11 without locating the sensor in the reservoir 11. In addition, according to the present embodiment, the determination is made taking factors of the pressure loss into consideration. Accordingly, it is possible to more accurately recognize the change in the liquid level (x) in the reservoir 11.

Figure 10:
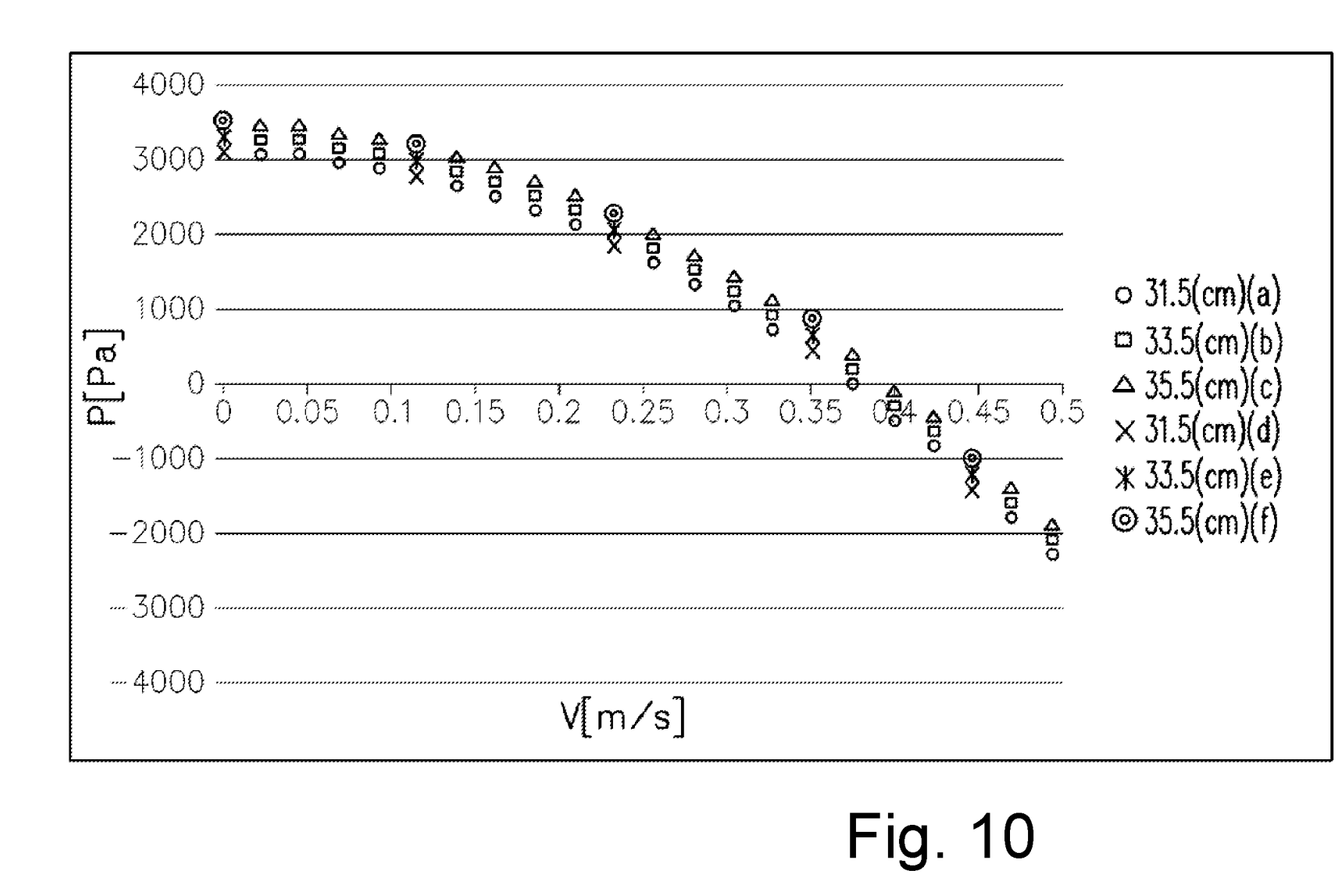
FIG. 10 is a numerical plot illustrating results of theoretical values and experimental values (experiment using water) of "zx–zy", based on "blood reserve level estimation expression data" in FIG. 4.

FIG. 10 is a schematic view illustrating results of theoretical values and experimental values (experiment using water) of "zx−zy", based on "blood reserve level estimation expression data" in FIG. 4. As illustrated in FIG. 10, theoretical values (a), (b), and (c) are plotted (drawn) as illustrated in FIG. 10 by using a relationship between the flow velocity (v) and the pressure (p) (wherein the pressure loss (f) is set to 41920.546). On the other hand, experimental values (d), (e), and (f) are similarly plotted. As can be understood from these, the experimental values substantially overlap with the theoretical values, and the experimental results as the theoretical result are obtained. In this manner, correctness of the expression "blood reserve level estimation expression data" in FIG. 4 is verified.

Incidentally, subsequent to ST7, the process proceeds to ST8. In ST8, a "blood reserve level hazard area determination processing unit (program) 46" in FIG. 4 is operated so as to refer to the "blood reserve level estimation data storage unit 45" and a "blood reserve hazard level data storage unit 47". In this manner, it is determined whether or not a value of the blood reserve level estimation data is included in a value of blood reserve hazard level data.

In ST9, when it is determined that the value of the blood reserve level estimation data is included in the value of the blood reserve hazard level data, the process proceeds to ST10. In ST10, "warning/alarm" is displayed on the touch panel 21 of the controller 20. Therefore, the operator of the extracorporeal circulator 2 can quickly and reliably recognize that the liquid level (x) of the blood inside the reservoir 11 is abnormally lowered.

On the other hand, in ST9, when it is determined that the value of the blood reserve level estimation data is not included in the value of the blood reserve hazard level data, the process proceeds to ST11. In ST11, it is determined whether or not a plurality of the "blood reserve level estimation data items" are present in the "blood reserve level estimation data storage unit 45" in FIG. 4. When a plurality of the "blood reserve level estimation data items" are present, the process proceeds to ST12.

In ST12, a "blood reserve level change amount estimation processing unit (program) 51" in FIG. 5 is performed so as to refer to the "flow rate sensor 14" and a "reservoir cross-sectional area data storage unit 52" in FIG. 5. Cross-sectional area data on the reservoir 11 in FIG. 1 is stored in the "reservoir cross-sectional area data storage unit 52". That is, based on the "flow velocity data" of the "flow rate sensor 14" and the cross-sectional area data of the "reservoir 11", "blood reserve level change amount estimation data" which is a height change amount of the liquid level of the blood in the reservoir 11 during a predetermined time can be obtained. In addition, safety margin data at a predetermined rate (for example, 1.5 times) is added to the change amount. In this manner, "margin-provided blood reserve level change amount estimation data (Z caution)" is generated and stored in a "margin-provided blood reserve level change amount estimation data storage unit 53" in FIG. 5.

In this manner, it is possible to generate data relating to a normal change amount and the safety margin data of the liquid level of the blood inside the reservoir 11 per predetermined time when the blood inside the reservoir 11 is supplied at the flow velocity. That is, in a case where the change amount per predetermined time exceeds the normal change amount and the safety margin (for example, 1, 5 times), it can be determined as abnormality (an example of the changed abnormality information).

For example, in some cases, the first intermediate tube 12 may be pinched with forceps in order to adjust the flow rate in an intermediate portion of a circuit of the extracorporeal circulator 2. In this case, the information relating to the pressure loss coefficient is changed, and thus, it becomes difficult to generate accurate "blood reserve level estimation data. In this regard, according to the present embodiment, it is possible to determine the occurrence of the abnormality. Specifically, the process is as follows.

In ST13, a "blood reserve level actual change amount data generation processing unit (program) 54" in FIG. 5 is performed so as to refer to the "blood reserve level estimation data storage unit 45". Based on the distance (height) between a plurality of the liquid levels (x) and the pressure measurement point (y) of the pressure sensor 14, that is, the "blood reserve level estimation data" which is "zx−zy" and the time data, "blood reserve level actual change amount data ($\Delta$(zx−zy))" which is data on the amount of change in the distance (height) per predetermined time is calculated and stored in a "blood reserve level actual change amount data storage unit 55".

That is, based on the actual data of the "blood reserve level estimation data storage unit 45", it is determined whether or not "zx−zy" is changed and how much is the change amount, and a determination result is stored in the "blood reserve level actual change amount data storage unit 55".

Next, the process proceeds to ST14. In ST14, a "blood reserve level change amount abnormality determination processing unit (program) 56" in FIG. 5 is performed so as to refer to the "blood reserve level actual change amount data storage unit 55" and the "the margin-provided blood reserve level change amount estimation data storage unit 53". It is determined whether or not the "blood reserve level actual change amount data ($\Delta$(zx−zy))" falls within or beyond a range of "margin-provided blood reserve level change amount estimation data (Z caution)".

Next, in ST15, if it is determined that "$\Delta$(zx−zy)$\geq$Z, caution" (an example of the changed abnormality information), "warning/alarm" is displayed on the touch panel 21 of the controller 20 in ST16. In this case, an operator of the extracorporeal circulator 2 recognizes a situation where accurate "blood reserve level estimation data" is less likely to be generated, and the operator can quickly perform required measures such as changing the information on the pressure loss coefficient.

On the other hand, if "Δ(zx−zy)≥Z, caution" is not satisfied in ST15, that is, if it is determined that there is no abnormality, the process proceeds to ST17. In ST17, a message of "is any change provided between the liquid level (x) and the pressure measurement point (y)?" is displayed on the touch panel 21.

In ST18, when it is determined that "some change is provided", for example, that the flow rate is slightly adjusted with forceps, the process proceeds to ST19. In ST19, if a message of "Is the change to be maintained?" is displayed on the touch panel 21 and if the change is not maintained in ST20, a message of "Please dismiss the change in the circuit" is displayed on the touch panel 21 in ST21. Therefore, in a case where the flow rate is slightly adjusted with the forceps, the forceps are removed as early as possible. In this manner, the controller 20 can prevent poor accuracy in the "blood reserve level estimation".

Incidentally, the present invention is not limited to the above-described embodiments.

What is claimed is:

1. An extracorporeal blood circulation system for monitoring blood level in a reservoir temporarily storing the blood, comprising:
    a memory storage unit for storing blood pressure measurements from a pressure sensor monitoring a blood pressure within a tube unit conveying blood from the reservoir relative to atmosphere;
    an input device configured for operator entry of an initial height data of the blood stored in the reservoir; and
    a processing unit that detects a height of a top surface of the blood stored in the reservoir as a change in height from the initial height data based on changes in the blood pressure measurements and a conservation of mechanical energy of a blood flow inside the tube unit;
    wherein the memory storage unit further stores blood density information, gravitational acceleration information, and flow velocity information from a flow rate measurement unit which is located in the tube unit;
    wherein the processing unit 1) determines a calculated liquid level energy at the top surface of the blood stored in the reservoir based on the blood density information, the gravitational acceleration information, and the flow velocity information, 2) determines a measured energy at the tube unit based on the flow velocity information, the pressure measurements, the blood density information, and the gravitational acceleration information, and 3) determines the height based on the calculated liquid level energy and the measured energy;
    wherein the height is further based on a pressure loss coefficient characterizing a pressure loss from the top surface of the blood stored in the reservoir to the tube unit;
    wherein the processing unit generates corrected pressure loss coefficient information based on an average of a plurality of pressure loss coefficients determined in time series; and
    wherein the height is based on the corrected pressure loss coefficient information.

2. The extracorporeal blood circulation system according to claim 1, wherein the processing unit detects occurrence of a height indicating an abnormality, and generates a notification upon detection of the occurrence of abnormality.

3. An extracorporeal blood circulator comprising:
    a blood reservoir for storing blood;
    a tube unit conveying the blood from the reservoir;
    an input device configured for operator entry of an initial height data of the blood stored in the reservoir;
    a pressure measurement unit coupled to the tube unit generating blood pressure measurements of a blood pressure within the tube unit relative to atmosphere;
    an artificial lung unit that performs gas exchange on the conveyed blood of a target person;
    a memory storage unit for storing blood pressure measurements;
    a processing unit that detects a height of a top surface of blood stored in the reservoir as a change in height from the initial height data based on changes in the blood pressure measurements and a conservation of mechanical energy of a blood flow inside the tube unit; and
    wherein the height is based on the corrected pressure loss coefficient information;
    wherein the memory storage unit further stores blood density information, gravitational acceleration information, and flow velocity information from the flow rate measurement unit;
    wherein the processing unit 1) determines a calculated liquid level energy at the top surface of the blood stored in the reservoir based on the blood density information, the gravitational acceleration information, and the flow velocity information, 2) determines a measured energy at the tube unit based on the flow velocity information, the pressure measurements, the blood density information, and the gravitational acceleration information, and 3) determines the height based on the calculated liquid level energy and the measured energy;
    wherein the height is further based on a pressure loss coefficient characterizing a pressure loss from the top surface of the blood stored in the reservoir to the tube unit;
    wherein the processing unit generates corrected pressure loss coefficient information based on an average of a plurality of pressure loss coefficients determined in time series; and
    wherein the height is based on the corrected pressure loss coefficient information.

4. The extracorporeal blood circulator according to claim 3, wherein the processing unit detects occurrence of a height indicating an abnormality, and generates a notification upon detection of the occurrence of abnormality.

5. A method of operating an extracorporeal blood circulation system, comprising:
    temporarily storing blood in a reservoir;
    manually indicating an initial height data of the blood using a height indicator disposed on the reservoir;
    conveying blood from the reservoir via a tube unit;
    generating blood pressure measurements of a blood pressure within the tube unit relative to atmosphere; and
    detecting a height of a top surface of the blood stored in the reservoir as a change in height from the initial height data based on changes in the blood pressure measurements and a conservation of mechanical energy of a blood flow inside the tube unit, wherein the detecting step is comprised of:
        measuring a flow velocity in the tube unit;
        determining a blood density;
        determining gravitational acceleration information;

determining a calculated liquid level energy at the top surface of the blood stored in the reservoir based on the blood density information, the gravitational acceleration information, and the flow velocity information;

determining a measured energy at the tube unit based on the flow velocity information, the pressure measurements, the blood density information, and the gravitational acceleration information; and determining the height based on the calculated liquid level energy, the measured energy, and a pressure loss coefficient information characterizing a pressure loss from the top surface of the blood stored in the reservoir to the tube unit;

wherein the corrected pressure loss coefficient information is based on an average of a plurality of pressure loss coefficients determined in time series.

\* \* \* \* \*